United States Patent
Enomoto et al.

(10) Patent No.: US 10,551,233 B2
(45) Date of Patent: *Feb. 4, 2020

(54) AIR FLOW RATE MEASUREMENT DEVICE

(71) Applicant: DENSO CORPORATION, Kariya, Aichi-pref. (JP)

(72) Inventors: Takashi Enomoto, Kariya (JP); Keisuke Itakura, Kariya (JP)

(73) Assignee: DENSO CORPORATION, Kariya (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/754,671

(22) PCT Filed: Dec. 12, 2016

(86) PCT No.: PCT/JP2016/086859
§ 371 (c)(1),
(2) Date: Feb. 23, 2018

(87) PCT Pub. No.: WO2017/110541
PCT Pub. Date: Jun. 29, 2017

(65) Prior Publication Data
US 2018/0245962 A1    Aug. 30, 2018

(30) Foreign Application Priority Data
Dec. 22, 2015 (JP) ................ 2015-249666

(51) Int. Cl.
*G01F 1/692*    (2006.01)
*G01N 27/22*    (2006.01)

(52) U.S. Cl.
CPC ........... *G01F 1/692* (2013.01); *G01N 27/225* (2013.01)

(58) Field of Classification Search
CPC .............. G01F 1/692; G01F 1/68; G01F 1/684
USPC ......................................... 73/29.02
See application file for complete search history.

(56) References Cited

U.S. PATENT DOCUMENTS

| | | | |
|---|---|---|---|
| 8,701,475 B2 * | 4/2014 | Kohno | G01F 1/684 73/114.33 |
| 2012/0198925 A1 * | 8/2012 | Saito | F02D 41/187 73/114.33 |
| 2013/0036806 A1 | 2/2013 | Kohno | |
| 2016/0290893 A1 | 10/2016 | Itakura | |
| 2018/0195984 A1 * | 7/2018 | Isoya | G01N 25/62 |
| 2018/0313681 A1 * | 11/2018 | Yogo | G01F 1/684 |

* cited by examiner

*Primary Examiner* — Nimeshkumar D Patel
*Assistant Examiner* — Jean F Morello
(74) *Attorney, Agent, or Firm* — Nixon & Vanderhye PC

(57) ABSTRACT

An air flow rate measurement device disposed in an intake passage by passing through an insertion hole of an intake pipe of an engine to communicate inside and outside includes: a case having a bypass channel, a part of air flowing through the intake passage flows into the bypass channel; a flow rate sensor arranged inside of the case, and having a flow rate detector which detects a flow rate of air flowing through the bypass channel; and a humidity sensor arranged outside of the case, and having a humidity detector which detects a humidity of air flowing through the intake passage. A surface of the humidity detector is arranged to oppose a wall of the case through a clearance.

9 Claims, 20 Drawing Sheets

(a)

(b)

AIR FLOW RATE MEASUREMENT DEVICE

CROSS REFERENCE TO RELATED APPLICATION

This application is the U.S. national phase of International Application No. PCT/JP2016/086859 filed Dec. 12, 2016, which designated the U.S. and claims priority to Japanese Patent Application No. 2015-249666 filed on Dec. 22, 2015, the entire contents of each of which are incorporated herein by reference.

TECHNICAL FIELD

The present disclosure relates to an air flow rate measurement device that measures a humidity of air in addition to a flow rate of air drawn into an engine.

BACKGROUND ART

Conventionally, an air flow rate measurement device is proposed (for example, refer to Patent Literature 1), which measures a humidity of air in addition to a flow rate of air drawn into an engine of a vehicle.

The air flow rate measurement device is installed by being inserted into an intake passage from an insertion hole of an intake pipe. The air flow rate measurement device includes a case forming a bypass channel which takes in a part of air flowing through the intake passage, a flow rate sensor installed in the case, and a humidity sensor installed outside of the case.

Meanwhile, when heat of the engine gets across to the case, a sensing part of the humidity sensor may receive radiant heat from the outer wall of the case. Especially, in case where the sensor is an electric capacitance type humidity sensor, if the temperature rises, the amount of moisture existing in air becomes different while the relative humidity is the same. For this reason, the accuracy for measuring the humidity may be lowered by the radiant heat from the outer wall of the case.

Then, in the air flow rate measurement device of Patent Literature 1, the humidity sensor is installed so that the sensing part is located to face an opposite side opposite from the outer wall of the case so as to reduce the influence of the radiant heat from the outer wall of the case.

However, when the sensing part of the humidity sensor is attached to the air flow rate measurement device to face outward of the case, the sensing part may be damaged. Specifically, the surface of the sensing part may contact the inner wall of the insertion hole, when the air flow rate measurement device is inserted into the intake passage to pass through the insertion hole from the outer side of the intake pipe.

Then, in the air flow rate measurement device of Patent Literature 1, a protection component which protects the surface of the sensing part is installed on the outer side of the humidity sensor. The case has a fitting part fitted with the inner wall of the insertion hole of the intake pipe, and a main body extending from the lower end of the fitting part into the intake passage. The protection component is provided to project from the lower end of the fitting part in a direction parallel to the outer surface of the main body.

However, since the protection component is provided to project outward from the case in the conventional air flow rate measurement device, the protection component becomes a resistance for the air passing outside of the case, such that the pressure loss of the air flowing through the intake passage increases.

Moreover, since a space for installing the protection component is needed on the lower side of the fitting part, the size of the fitting part in the width direction becomes large on the outer side of the case in the width direction. For this reason, the size of the case increases.

PRIOR ART LITERATURES

Patent Literature

Patent Literature 1: JP 5445535 B

SUMMARY OF INVENTION

It is an object of the present disclosure to provide an air flow rate measurement device which can accurately measure a humidity of air in addition to a flow rate of air without causing increase in size of a case and in pressure loss of air flowing through an intake passage.

According to an aspect of the present disclosure, in an air flow rate measurement device installed by being inserted into an intake passage from an insertion hole of an intake pipe of an engine, a surface of a humidity detector is arranged to oppose a wall of a case. Moreover, a clearance is defined between the surface of the humidity detector and the wall of the case.

Therefore, when inserting the air flow rate measurement device into the intake passage from the outer side of the intake pipe, the surface of the humidity detector can be prevented from contacting the inner wall of the insertion hole, without providing a protection component, which protects the surface of the humidity detector, to the case.

Accordingly, the humidity of air and the flow rate of air can be measured with sufficient accuracy, without causing increase in size of the case and increase in pressure loss of air flowing through the intake passage.

DESCRIPTION OF EMBODIMENTS

Figure 1:
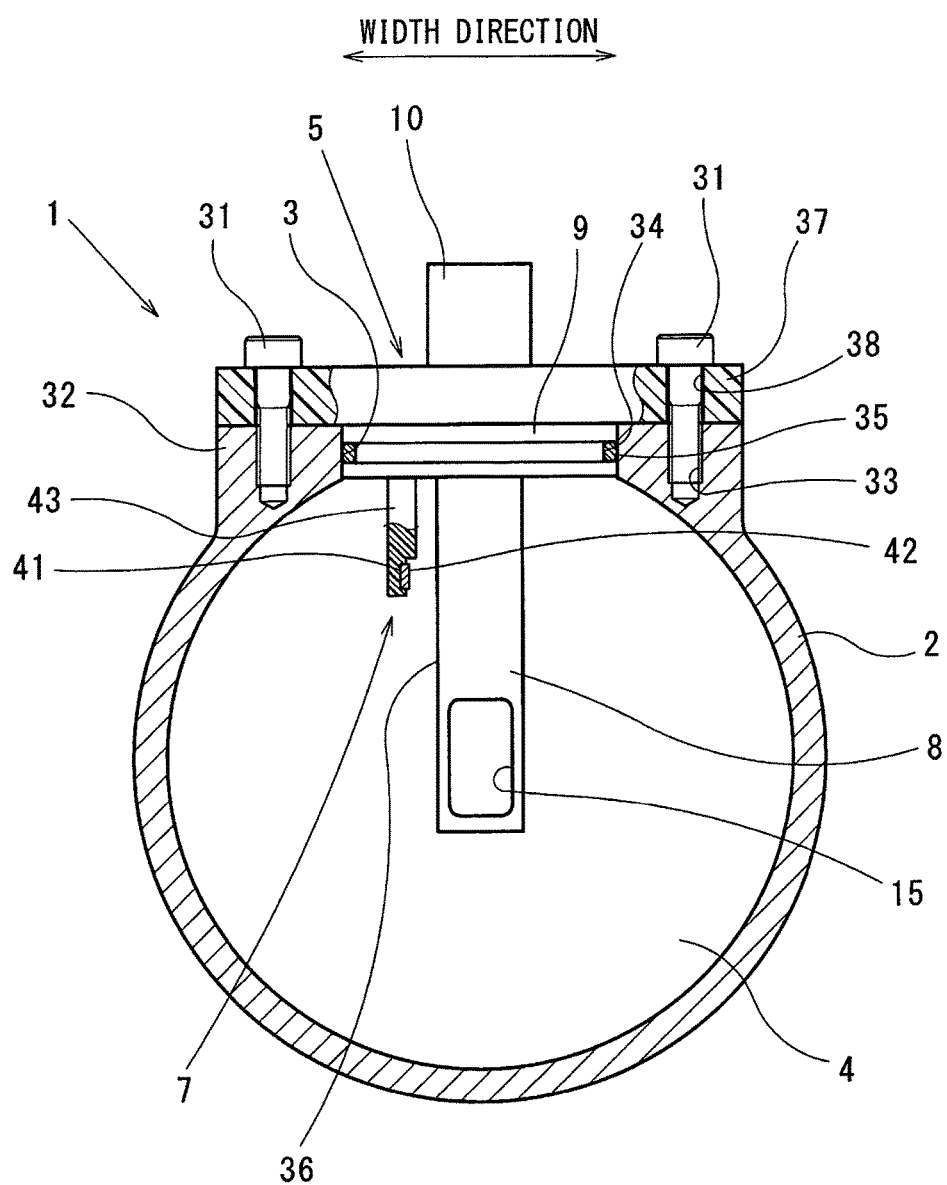
FIG. 1 is a front view illustrating an air flow rate measurement device attached to an intake pipe (according to a first embodiment).
Figure 2:
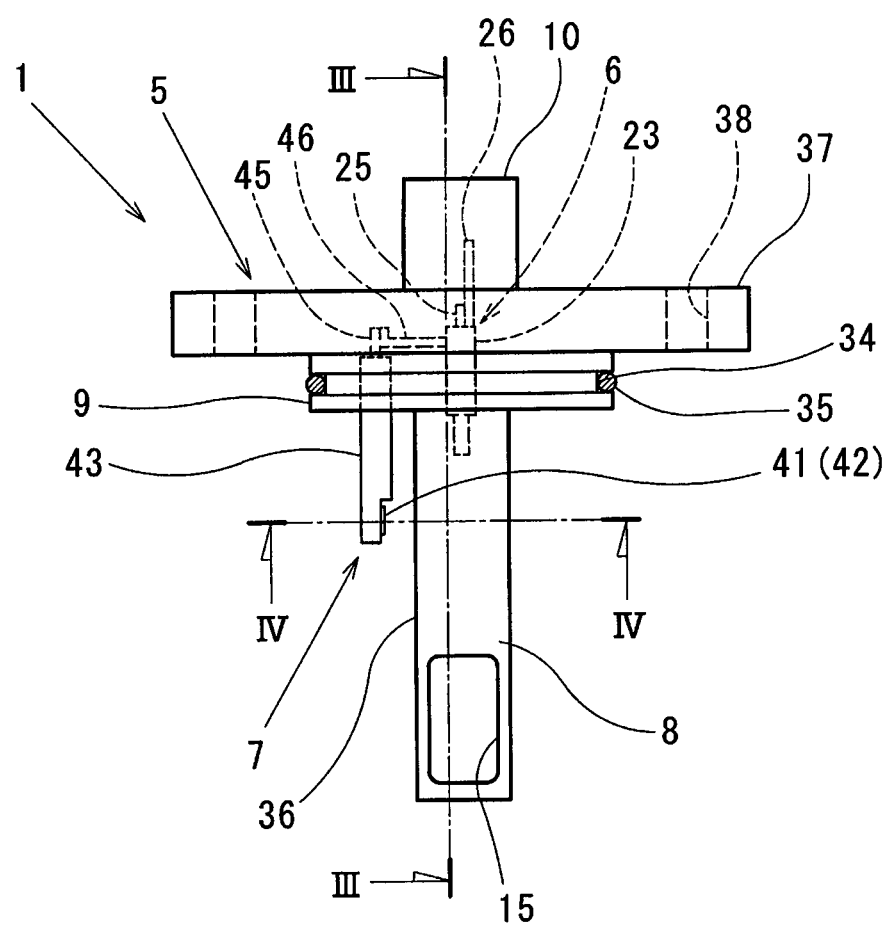
FIG. 2 is a front view illustrating the air flow rate measurement device (of the first embodiment).
Figure 3:
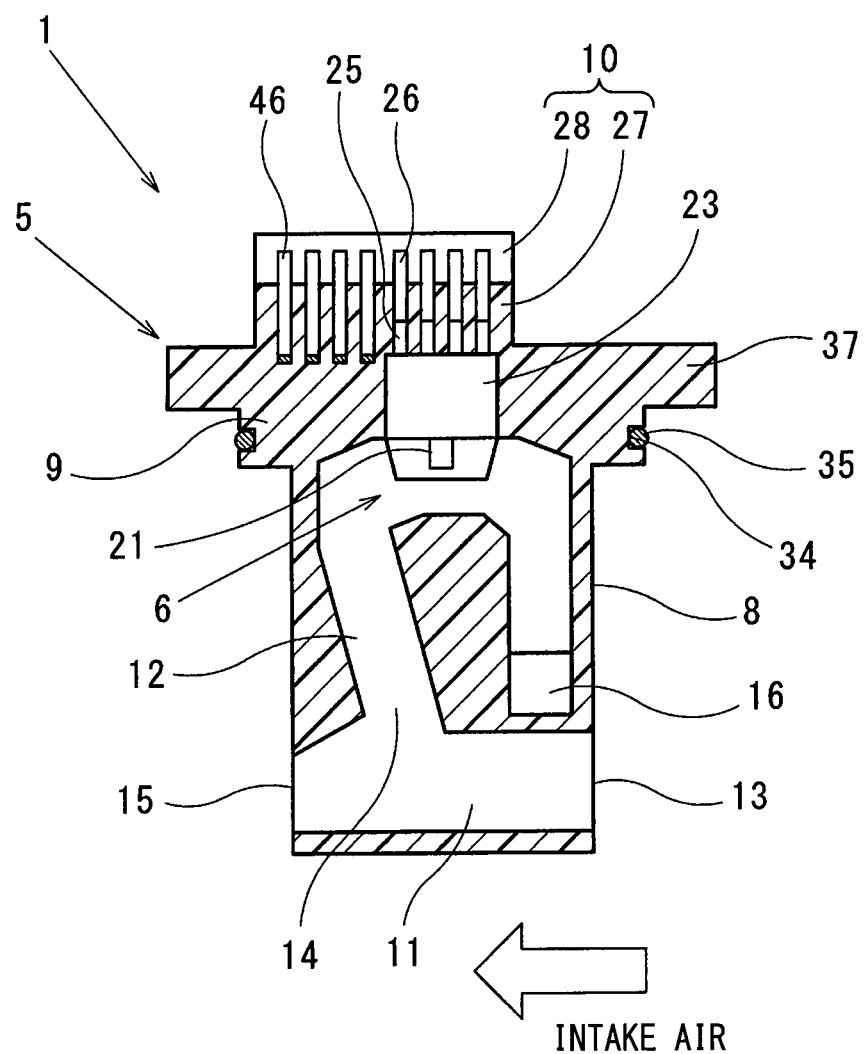
FIG. 3 is a sectional view taken along a line III-III of FIG. 2 (of the first embodiment).
Figure 4:
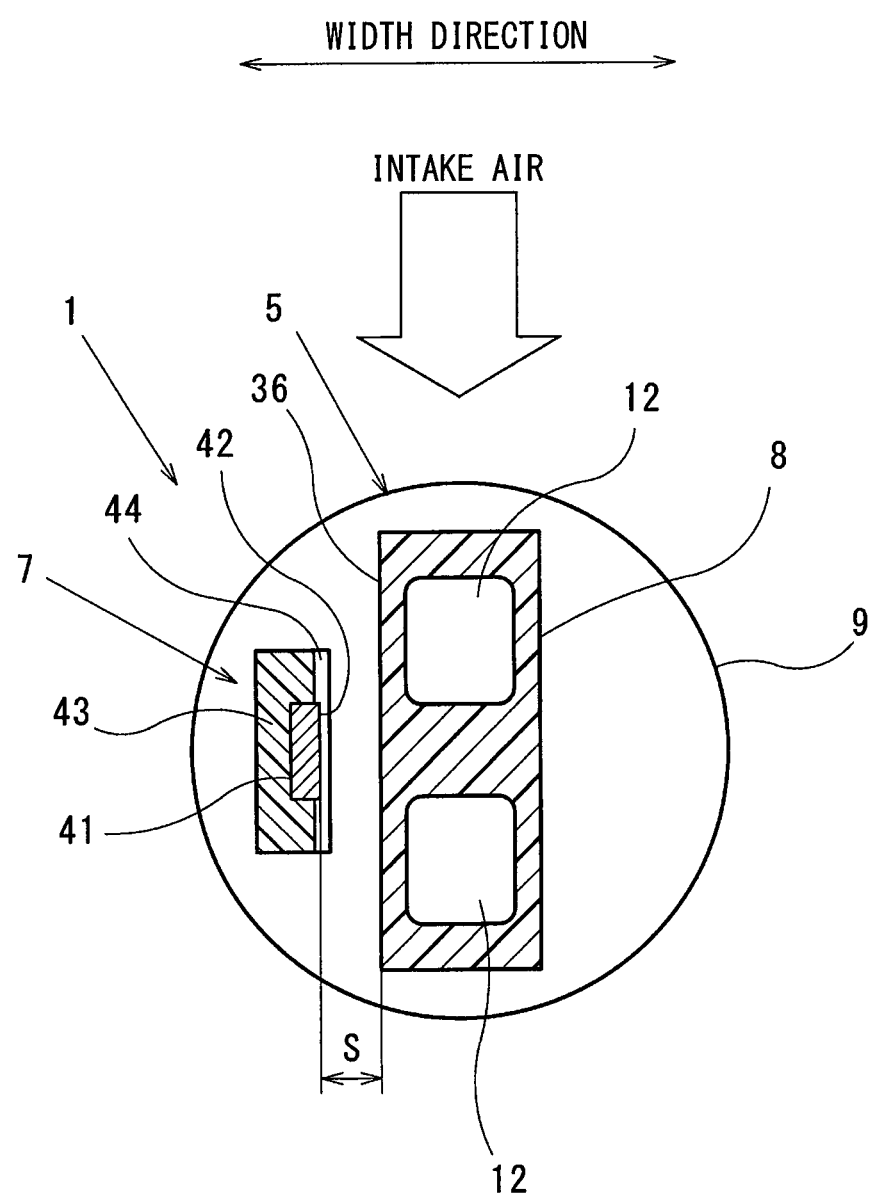
FIG. 4 is a sectional view taken along a line IV-IV of FIG. 2 (of the first embodiment).
Figure 5:
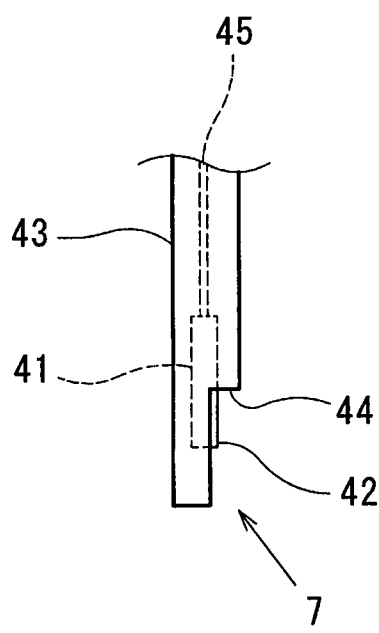
FIG. 5 includes (a) a side view illustrating a humidity sensor, and (b) a plan view of the humidity sensor (of the first embodiment).
Figure 5:
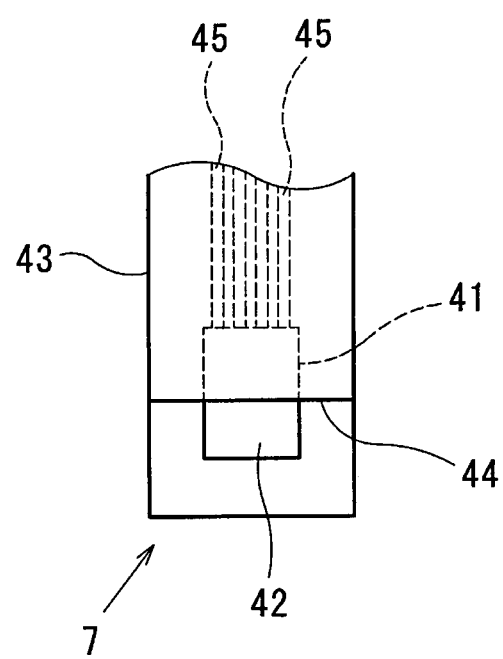
Figure 6:
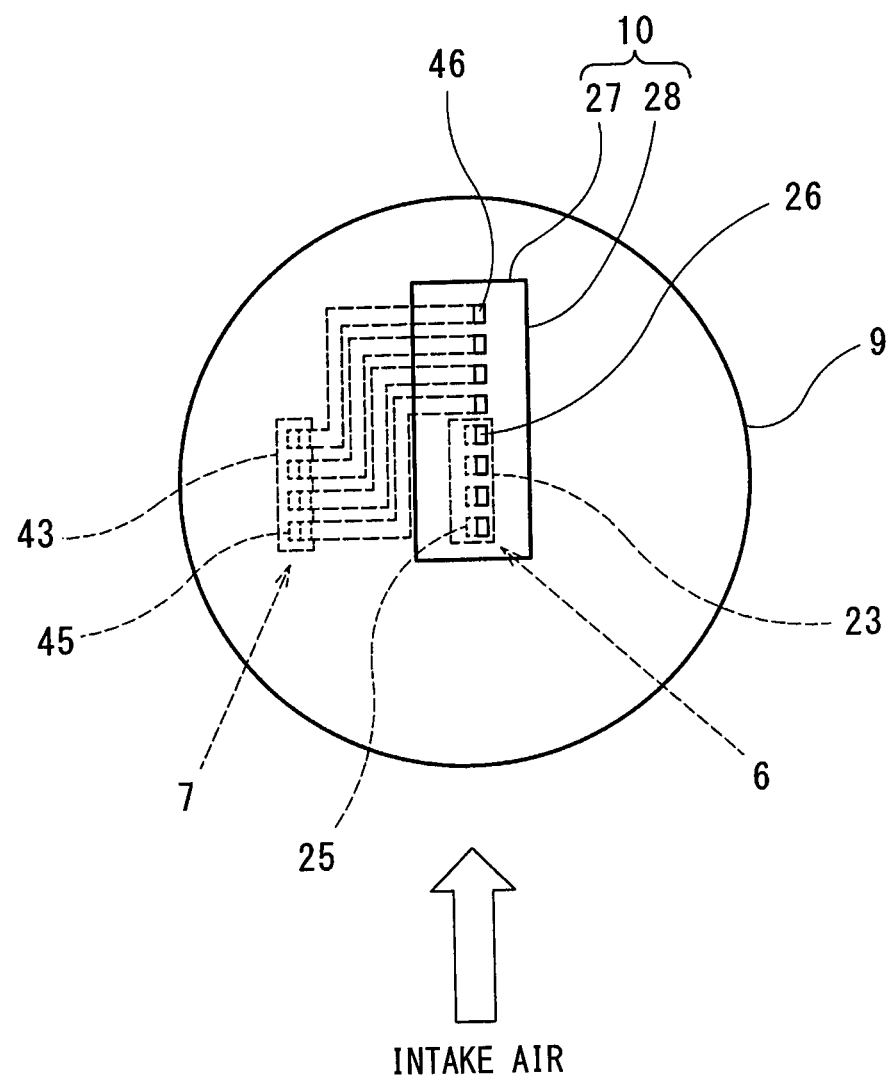
FIG. 6 is a plan view illustrating the air flow rate measurement device (of the first embodiment).

Hereafter, embodiments are explained referring to the drawings.

[First Embodiment]

FIG. 1 through FIG. 6 illustrate a first embodiment.

An air flow rate measurement device 1 of this embodiment is used as an airflow meter which measures a flow rate of air (hereafter, may be called as intake air) drawn into a cylinder of an engine for a vehicle.

The air flow rate measurement device 1 is disposed in an intake passage 4 by being inserted to pass through an insertion hole 3 from outside of an intake pipe 2 of the engine. The air flow rate measurement device 1 includes a case 5 fixed on the intake pipe 2 to project into the intake passage 4 by passing through the insertion hole 3, a flow rate sensor 6 which detects a flow rate of intake air flowing inside of the case 5, and a humidity sensor 7 which detects a humidity of intake air flowing through the intake passage 4.

The case 5 includes a main body 8 installed in the intake passage 4, a fitting part 9 defined in the upper side of the main body 8, as illustrated, and a connector case 10 defined in the upper side of the fitting part 9.

A bypass channel 11 and a bypass channel 12 are formed inside of the main body 8, and a part of the intake air flowing through the intake passage 4 is taken into the bypass channels 11 and 12.

The connector case 10 is formed integrally with the main body 8 through the fitting part 9. The connector case 10 is arranged outside of the intake pipe 2.

A channel inlet 13 is defined at the upstream end of the bypass channel 11, and is open to face the upstream side of the intake passage 4. A branch part 14 is formed in the bypass channel 11, where the bypass channel 12 branches from the bypass channel 11. A channel exit 15 is defined at the downstream end of the bypass channel 11 to discharge the taken-in air to the downstream side of the intake passage 4, and a channel exit 16 is defined at the downstream end of the bypass channel 12 to discharge the taken-in air to the downstream side of the intake passage 4.

The bypass channel 11 is formed parallel to the flow direction of the intake air flowing through the intake passage 4. The intake air taken in from the channel inlet 13 passes through the bypass channel 11, and is discharged from the channel exit 15.

The intake air taken in from the branch part 14 passes through the bypass channel 12 and is discharged from the channel exit 16. The bypass channel 12 defines a bending channel where the flow direction of the intake air changes by 180 degrees or more.

The flow rate sensor 6 includes a flow rate detector (henceforth, sensing part) 21 arranged to be exposed to the bypass channel 12. The flow rate sensor 6 is a package product gas-tightly sealed with a sealing agent 23 such as mold resin in the state where a part of the sensing part 21 is exposed.

The sensing part 21 outputs an electric signal corresponding to the flow rate of the intake air passing through the bypass channel 12 to an electronic control unit (hereafter referred to ECU).

The sensing part 21 includes a sensor chip in which a silicon semiconductor board (hereafter referred to silicon substrate) shaped in a plate is arranged to be parallel to the flow direction of the intake air flowing through the bypass channel 12, and a membrane is formed on the surface of the silicon substrate.

A thin-film resistance object (henceforth, heater resistor) is arranged in the center of the membrane of the sensor chip, and emits heat at high temperature when a heating current is supplied.

Plural thin-film resistance objects (henceforth, air temperature resistor) are arranged on the upstream side and the downstream side in the flow direction of the intake air, relative to the heater resistor at the center, and detect the temperature of air on the upstream side and the downstream side of the membrane.

A thin-film resistance object (henceforth, intake-air temperature resistor) is arranged at a place not affected by the heater resistor, and detects the temperature of the surrounding air.

The flow rate sensor 6 includes a processing circuit chip which processes the input/output signal of the sensing part 21.

The processing circuit chip is mounted on each island of a lead frame with the sensing part 21.

The lead frame is formed in a predetermined shape by press processing and/or etching processing a metal conductor board. The lead frame is gas-tightly sealed with the sealing agent 23 such as mold resin, with the sensing part 21 and the processing circuit chip. A part of the lead frame defines plural flow rate sensor terminals 25 arranged in parallel to the flow direction of the intake air.

A heater drive circuit unit is mounted on the processing circuit chip of the flow rate sensor 6, and sets the heater resistor to have a temperature higher than the temperature of the surrounding air by a certain constant value. The air temperature resistor detects the temperature distribution on the membrane of the sensor chip.

The flow rate sensor 6 calculates a difference between the air temperature detected with the air temperature resistor on the upstream side of the heater resistor and the air temperature detected with the air temperature resistor on the downstream side of the heater resistor, to measure the flow rate of intake air.

The plural flow rate sensor terminals 25 are plate-shaped lead terminals.

One end of each flow rate sensor terminal 25 is electrically connected with an electrode part (hereafter, electrode pad group) of the processing circuit chip through a bonding wire.

The other end of each flow rate sensor terminal 25 is electrically connected with one end of each connector terminal 26 using, for example, welding.

The plural flow rate sensor terminal 25 and the plural connector terminals 26 are manufactured by punching a metal thin board which has conductivity with a press-molding machine, and by bending at a predetermined part simultaneously or after the punching.

The other end of each flow rate sensor terminal 25 is wired to the connector 27 of the connector case 10. A cavity 28 is formed in the connector 27, and is fitted with an external apparatus such as the other connector.

The plural connector terminals 26 are arranged to be parallel to the flow direction of intake air, similarly to the plural flow rate sensor terminals 25.

The other end of each connector terminal 26 is projected and exposed into the cavity 28 of the connector 27. Each connector terminal 26 configures an external connection terminal for being electrically connected with an external circuit such as ECU or external power supply through electric wires such as wire harness.

A cylindrical attachment boss part 32 is formed in the intake pipe 2, for fixing the air flow rate measurement device 1 with the bolt 31. The bolt 31 is engaged with a female thread hole 33 of the attachment boss part 32. Thereby, the case 5 is fixed to the attachment boss part 32.

A round insertion hole 3 is formed in the attachment boss part 32 to communicate the inside and the outside of the intake pipe 2. The insertion hole 3 has a hole width (also called as a hole diameter) in the width direction perpendicular to the flow direction of the intake air flowing through the intake passage 4.

The case 5 has the fitting part 9 which is gas-tightly connected with the inner wall (also called as an inner circumference surface) of the insertion hole 3. A circular circumferential groove 34 is formed around the outer circumference surface of the fitting part 9. An O ring 35 is fitted in the circumferential groove 34 to seal a clearance between the inner circumference surface of the insertion hole 3 and the outer circumference surface of the fitting part 9.

The case 5 has the outer wall 36, and intake air passes on the outer side of the outer wall 36.

The case 5 has a flange 37 located between the fitting part 9 and the connector case 10. The flange 37 has an insertion hole 38 through which the bolt 31 passes.

The humidity sensor 7 includes the humidity detector (henceforth, sensing part) 41 which detects the humidity of the intake air flowing through outside of the main body 8. The humidity sensor 7 is a package product gas-tightly sealed with the sealing agent 43, such as mold resin, in the state where the surface 42 of the sensing part 41 is exposed. That is, the surface 42 of the sensing part 41 is exposed from the surface of the sealing agent 43 through an opening 44 defined in the sealing agent 43.

The sensing part 41 is an electric capacitance type, for example, in which an insulated film is formed on the surface of a plate-shaped silicon semiconductor board (hereafter referred to as silicon substrate). A pair of comb-teeth electrodes are formed on the same surface of the insulated film to oppose with each other through a space. A protective film is formed on the comb-teeth electrodes. A humidity sensing film is formed on the protective film to cover the surface of both comb-teeth electrodes, such that the capacitance value changes according to the humidity.

The formation area of the humidity sensing film is defined as a humidity sensing part which detects humidity. A part of the humidity sensing part is the surface (also called as a humidity sensing surface) 42 of the sensing part 41 exposed in the intake passage 4.

When moisture permeates into the humidity sensing film, since the dielectric constant of the water molecule is large, the dielectric constant of the humidity sensing film also has a large change, according to the amount of the moisture permeating in the sensing part 41. As a result, the capacitance value between the comb-teeth electrodes also comes to change. Thus, since the capacitance value between the pair of comb-teeth electrodes changes in response to the change in humidity around the surface 42 of the sensing part 41, the humidity sensing part can detect the humidity based on the change in the capacitance value.

The humidity sensor 7 includes a processing circuit chip which processes the input/output signal of the sensing part 41.

The processing circuit chip is mounted on each island of a lead frame with the sensing part 41.

The lead frame is formed in a predetermined shape by press processing and/or etching processing a metal conductor board. The lead frame is gas-tightly sealed with the sealing agent 43 such as mold resin, with the sensing part 41 and the processing circuit chip. A part of the lead frame defines plural humidity sensor terminals 45 arranged in parallel to the flow direction of the intake air.

The plural humidity sensor terminals 45 are plate-shaped lead terminals.

One end of each humidity sensor terminal 45 is electrically connected with an electrode part (hereafter, electrode pad group) of the processing circuit chip through a bonding wire.

The other end of each humidity sensor terminal 45 is electrically connected with one end of plural connector terminals 46 using, for example, welding.

The plural humidity sensor terminal 45 and the plural connector terminals 46 are manufactured by punching a metal thin board which has conductivity with a press-molding machine, and by bending at a predetermined part simultaneously or after the punching.

The other end of each humidity sensor terminal 45 is wired to the connector 27.

The plural connector terminals 46 are arranged to be parallel to the flow direction of intake air, similarly to the plural humidity sensor terminals 45.

The other end of each connector terminal 46 is projected and exposed in the cavity 28 of the connector 27. Each connector terminal 46 configures an external connection terminal for being electrically connected with an external circuit such as ECU or an external power supply through electric wires such as wire harness.

The respective connector terminals 46 and the respective connector terminals 26 are arranged through a predetermined interval, so as to be integrally connected as package to an external apparatus. Moreover, the respective connector terminals 46 and the respective connector terminals 26 are arranged in parallel with the flow direction of intake air.

The connector case 10 has one connector 27 for making electric connection between the flow rate sensor 6 and the humidity sensor 7, and an external circuit.

The connector 27 is fabricated with insulated mold resin which forms the connector case 10. The connector 27 holds the plural flow rate sensor terminals 25 and the plural connector terminals 26 by an insert molding with mold resin. The connector 27 covers and protects each conduction junction between the flow rate sensor terminals 25 and the connector terminals 26.

The connector 27 holds the plural humidity sensor terminals 45 and the plural connector terminals 46 by an insert molding with mold resin. The connector 27 covers and protects each conduction junction between the humidity sensor terminals 45 and the connector terminals 46.

The surface 42 of the sensing part 41 is arranged to oppose the outer wall 36 of the case 5 through the clearance S.

A direction parallel to the flow direction of intake air flowing through the intake passage 4 is defined as a front-rear direction of the case 5, and a direction perpendicular to the front-rear direction of the case 5 is defined as a width direction of the case 5.

The clearance S is formed in a direction parallel to the width direction of the case 5. The clearance S is narrower than the hole diameter of the insertion hole 3. The clearance S has a dimension able to acquire a choking effect to increase the flow velocity of intake air by reducing the passage sectional area of the intake passage 4, and has a dimension able to reduce the influence of the radiant heat from the outer wall 36.

The clearance S is set within a range more than or equal to 0.5 mm and less than or equal to 10 mm.

According to the air flow rate measurement device 1 of this embodiment, the surface 42 of the sensing part 41 of the humidity sensor 7 is arranged to oppose the outer wall 36 of the case 5 through the clearance S. Therefore, the surface of the sensing part 41 cannot be damaged by contacting the inner wall of the insertion hole 3, without preparing a protection component for the case 5, which protects the surface of the sensing part 41, when the air flow rate measurement device 1 is attached into the intake passage 4 by passing through the insertion hole 3 from the outside of the intake pipe 2.

Therefore, the humidity of intake air and the flow rate of intake air can be measured with sufficient accuracy, without causing increase in size of the case 5 and without causing increase in pressure loss of the intake air flowing through the intake passage 4 of the intake pipe 2.

Moreover, in the air flow rate measurement device 1 of this embodiment, since the clearance S is made narrower than the hole width of the insertion hole 3, the distance between the surface 42 of the sensing part 41 of the humidity sensor 7 and the outer wall 36 of the case 5 can be shortened. For this reason, since the flow velocity of intake air can be raised by the choking effect, the scavenging speed of the intake air on the surface 42 of the sensing part 41 becomes large, such that the humidity can be measured with high responsivity.

Meanwhile, in case where the surface 42 of the sensing part 41 of the humidity sensor 7 is faced toward the outer wall of the case 5, if a clearance is narrower than 0.5 mm, the flow resistance of the intake air which passes on the outer side of the case 5 will become large, such that the flow velocity of intake air becomes low. Moreover, there is a possibility that the influence of the radiant heat from the outer wall 36 of the case 5 becomes large.

On the contrary, if the clearance is larger than 10 mm, there is a possibility that a worker's finger enters between the surface 42 of the sensing part 41 and the outer wall 36.

Then, in the air flow rate measurement device 1 of this embodiment, the upper limit of the distance between the surface 42 of the sensing part 41 and the outer wall 36 of the case 5 is set as 10 mm, and the lower limit is set as 0.5 mm. Thereby, the surface 42 of the sensing part 41 of the humidity sensor 7 can be prevented from being touched by a worker from the outer side. Moreover, the influence of the radiant heat received by the sensing part 41 from the outer wall 36 of the case 5 can be made small. Further, since the rise in the air temperature caused by the radiant heat from the outer wall 36 can be reduced, the error of the humidity detected by the electric capacitance type humidity sensor 7 can be reduced. Thereby, the measurement accuracy of the sensing part 41 can be restricted from being lowered.

Moreover, the flow resistance of intake air can be made small by setting the distance between the surface 42 of the sensing part 41 of the humidity sensor 7 and the outer wall 36 of the case 5 in a range from 0.5 mm to 10 mm. Thereby, since the flow velocity of intake air can be raised, the scavenging speed of air on the surface of the sensing part 41 becomes large, such that the humidity can be measured with high responsivity.

The surface of the sensing part 41 may be masked with a covering part shaped in a slit or a lattice for the purpose of protecting the sensing part 41 of the humidity sensor 7.

In case where the sensing part 41 is gas-tightly sealed with sealing resin, the covering part shaped in a slit or a lattice cannot integrally be molded with the case 5. For this reason, since it is necessary to bond another object to the case 5, the circumferential structure of the humidity sensor 7 becomes complicated and the cost increases.

Meanwhile, since it becomes difficult to scavenge air on the surface of the sensing part 41 by the intake air flowing through the intake passage 4 of the intake pipe 2, the responsivity in the humidity measurement may become low when the humidity changes.

According to the air flow rate measurement device 1 of this embodiment, the surface of the sensing part 41 is set to counter the case 5, thereby protecting the sensing part 41 without sacrificing the responsivity of humidity measurement.

In the air flow rate measurement device 1 of this embodiment, the respective flow rate sensor terminals 25 of the flow rate sensor 6 and the respective humidity sensor terminals 45 of the humidity sensor 7 are arranged in parallel to the flow direction of intake air. For this reason, it becomes easy to put in a jig, for example, in a welding process at a time of joining the flow rate sensor terminal 25 and the connector terminal 26 and at a time of joining the humidity sensor terminal 45 and the connector terminal 46.

Moreover, the one connector 27 is formed in the connector case 10 as package to hold the plural connector terminals 26 and 46 arranged parallel to the flow direction of intake air. Since the respective connector terminals 26 and the respective connector terminals 46 are wired to the same connector 27 in a concentrated manner, the number of components can be reduced, compared with a case where the connector terminal 26 and the connector terminal 46 are wired to separate connectors separate from each other.

[Second Embodiment]

Figure 7:
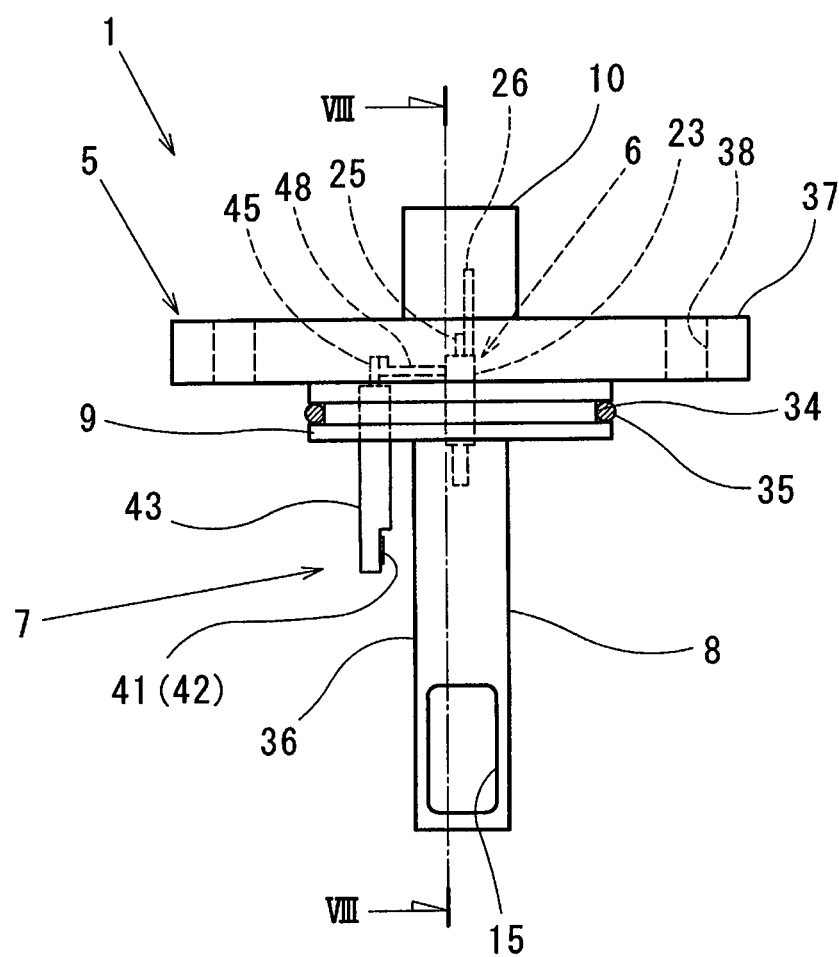
FIG. 7 is a front view illustrating an air flow rate measurement device (according to a second embodiment).
Figure 8:
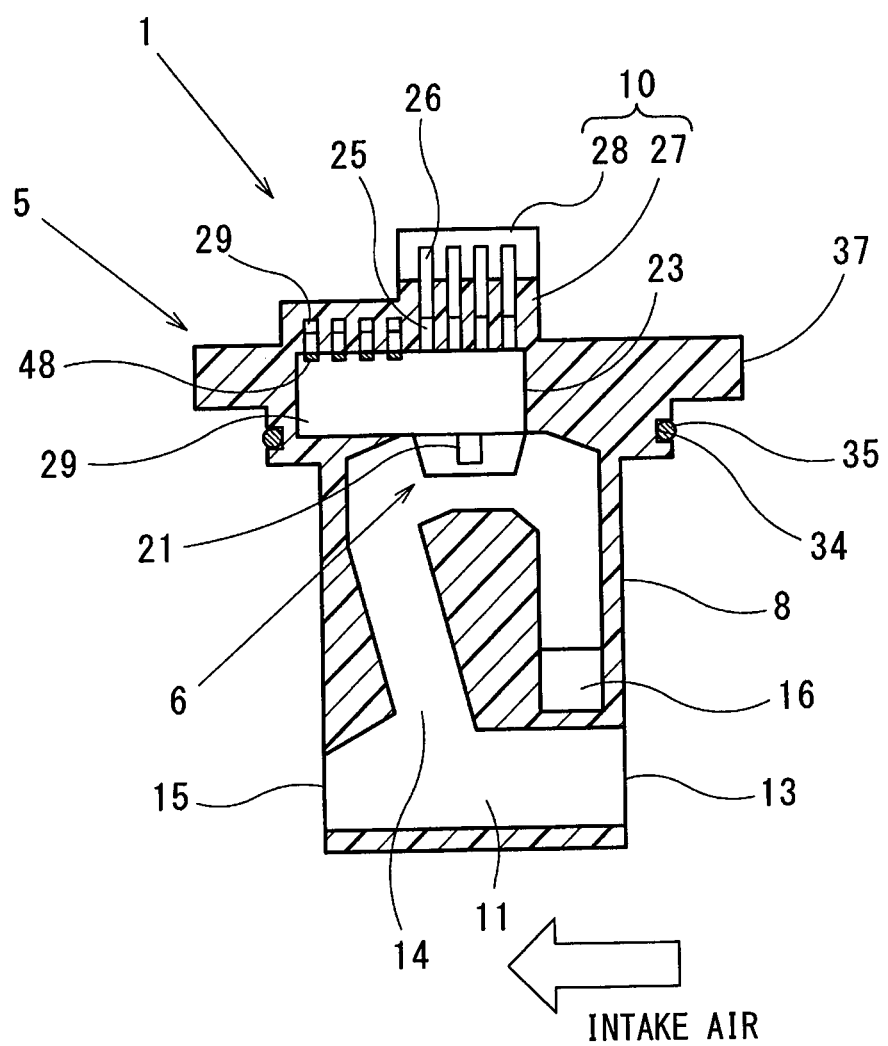
FIG. 8 is a sectional view taken along a line VIII-VIII of FIG. 7 (of the second embodiment).
Figure 9:
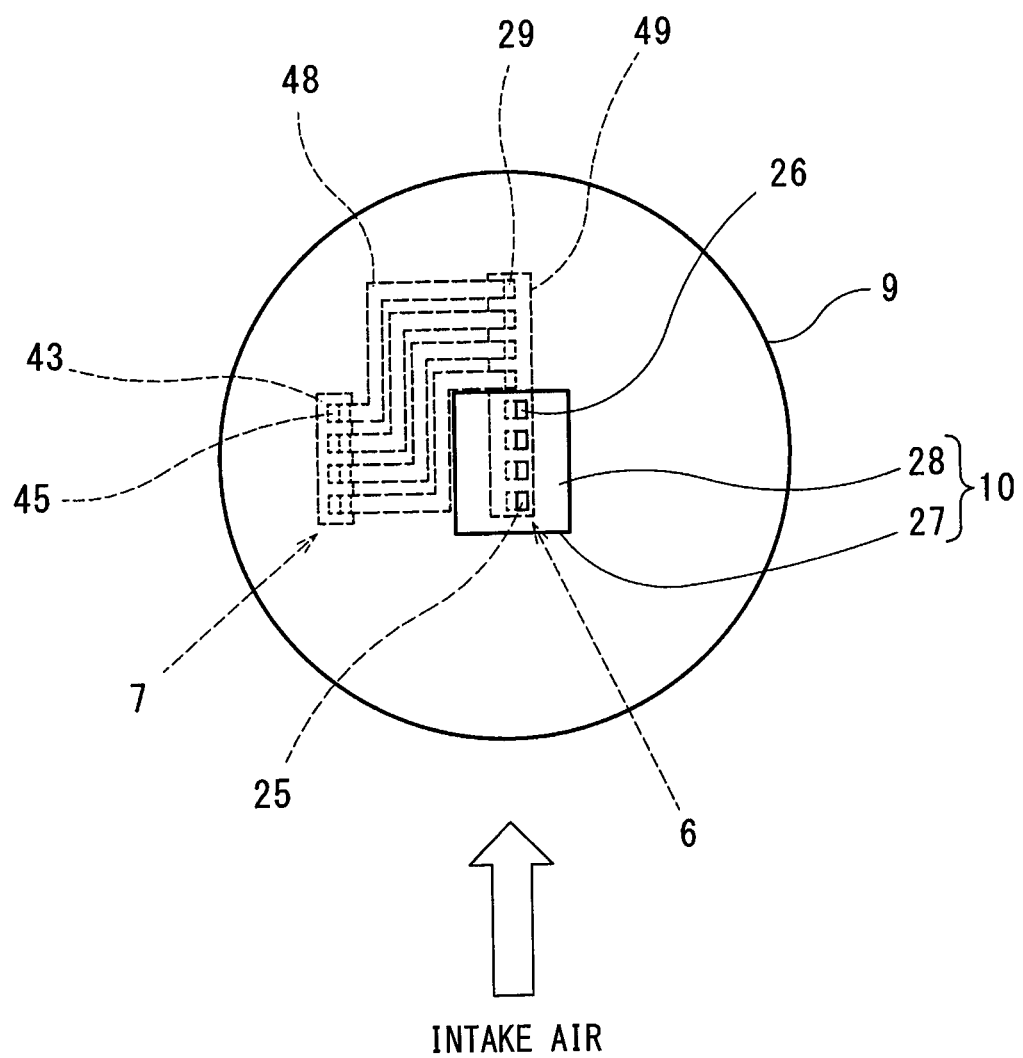
FIG. 9 is a plan view illustrating the air flow rate measurement device (of the second embodiment).

FIG. 7 through FIG. 9 illustrate a second embodiment.

The same mark as the first embodiment indicates the same configuration or function, and the redundant explanation is omitted.

The respective humidity sensor terminal 45 of the humidity sensor 7 of this embodiment is arranged in parallel with the flow direction of intake air, similarly to the first embodiment. The respective humidity sensor terminal 45 is electrically connected with one end of respective relay terminal 48 using, for example, welding. The other end of each relay terminal 48 is electrically connected with a processing circuit chip of the flow rate sensor 6 through a connecting terminal 29 of the flow rate sensor 6.

Similarly to the humidity sensor terminals 45, the relay terminals 48 are arranged parallel to the flow direction of intake air.

The connecting terminals 29 are arranged adjacent to the connector terminals 26. Similarly to the connector terminals 26, the connecting terminals 29 are arranged parallel to the flow direction of intake air. Similarly to the flow rate sensor terminal 25, the connecting terminal 29 defines a part of the lead frame of the flow rate sensor 6.

In addition, each of the connecting terminals 29 is held by a holding part 49 of the sealing agent 23.

The processing circuit chip of the flow rate sensor 6 is configured to output the output signal of the flow rate sensor 6 and the output signal of the humidity sensor 7 through the connector terminal 26 to ECU after taking in the output signal of the humidity sensor 7. The signal taken in from the humidity sensor 7 to the flow rate sensor 6 may be, for example, an analog signal, or a digital signal using I-squared-C (I2C) communication method. Moreover, the output of the flow rate sensor 6 and the humidity sensor 7 may be performed in combination of, for example, frequency and duty ratio, or a single edge nibble transmission (SENT) output may be used.

Since the connector terminal 26 of the flow rate sensor 6 and the connecting terminal 29 are arranged in parallel to the flow direction of intake air, the relay terminal 48 of the humidity sensor 7 is also arranged in parallel. Thereby, it becomes easy to put in a jig, for example, in a welding process, at a time of joining each flow rate sensor terminal 25 and each connector terminal 26, and at a time of joining each humidity sensor terminal 45 and each connecting terminal 29.

Moreover, the terminal number of the connector terminals 26, which are external connection terminals, can be reduced by taking the output signal of the humidity sensor 7 into the processing circuit chip of the flow rate sensor 6. Thereby, the number of components can be reduced, compared with a case where each connector terminal 26 of the flow rate sensor 6 and each connector terminal 46 of the humidity sensor 7 are wired in the connector 27.

As mentioned above, the same advantages can be obtained in the air flow rate measurement device 1 of this embodiment as the first embodiment.

[Third Embodiment]

Figure 10:
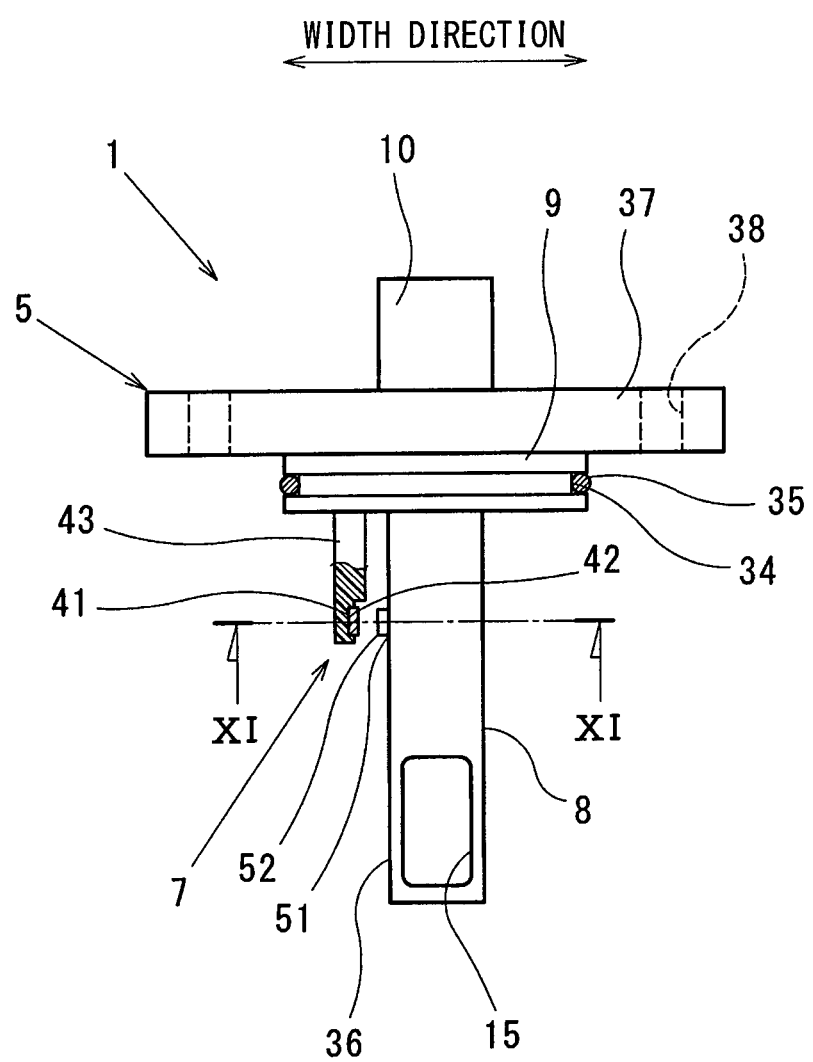
FIG. 10 is a front view illustrating an air flow rate measurement device (according to a third embodiment).
Figure 11:
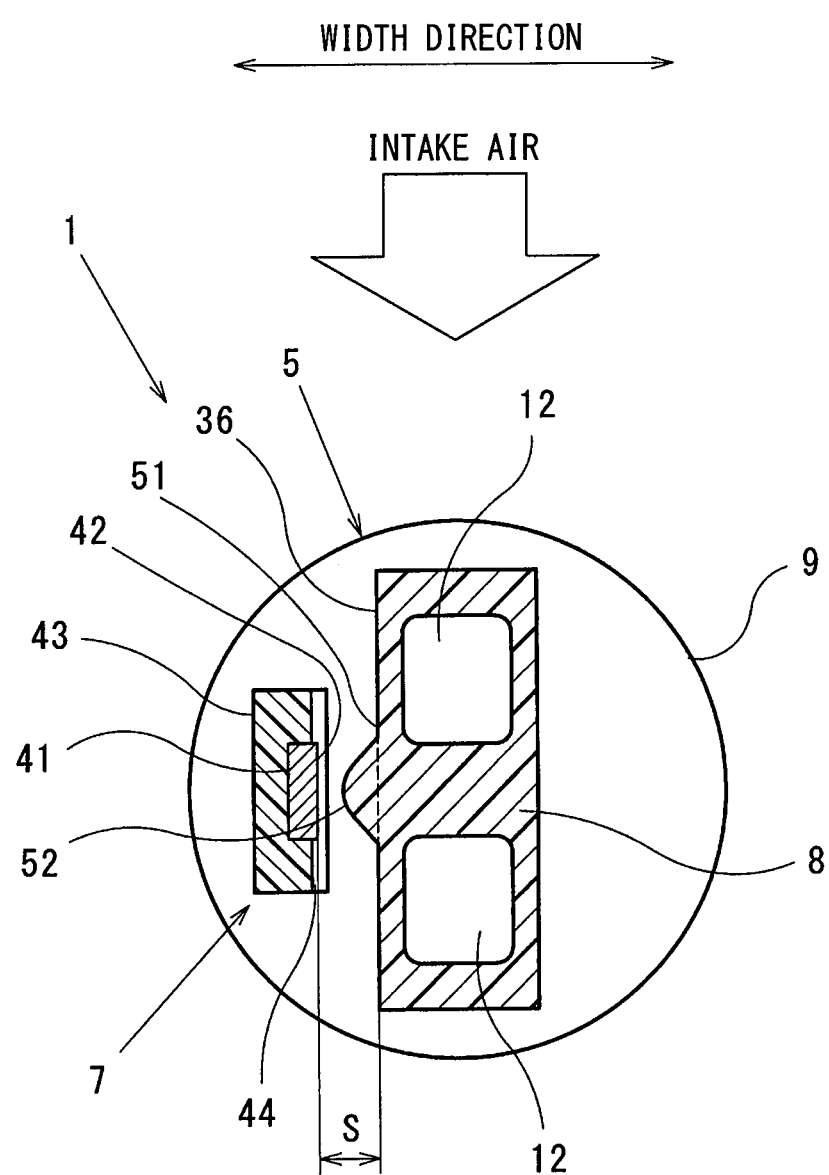
FIG. 11 is a sectional view taken along a line XI-XI of FIG. 10 (of the third embodiment).
Figure 12:
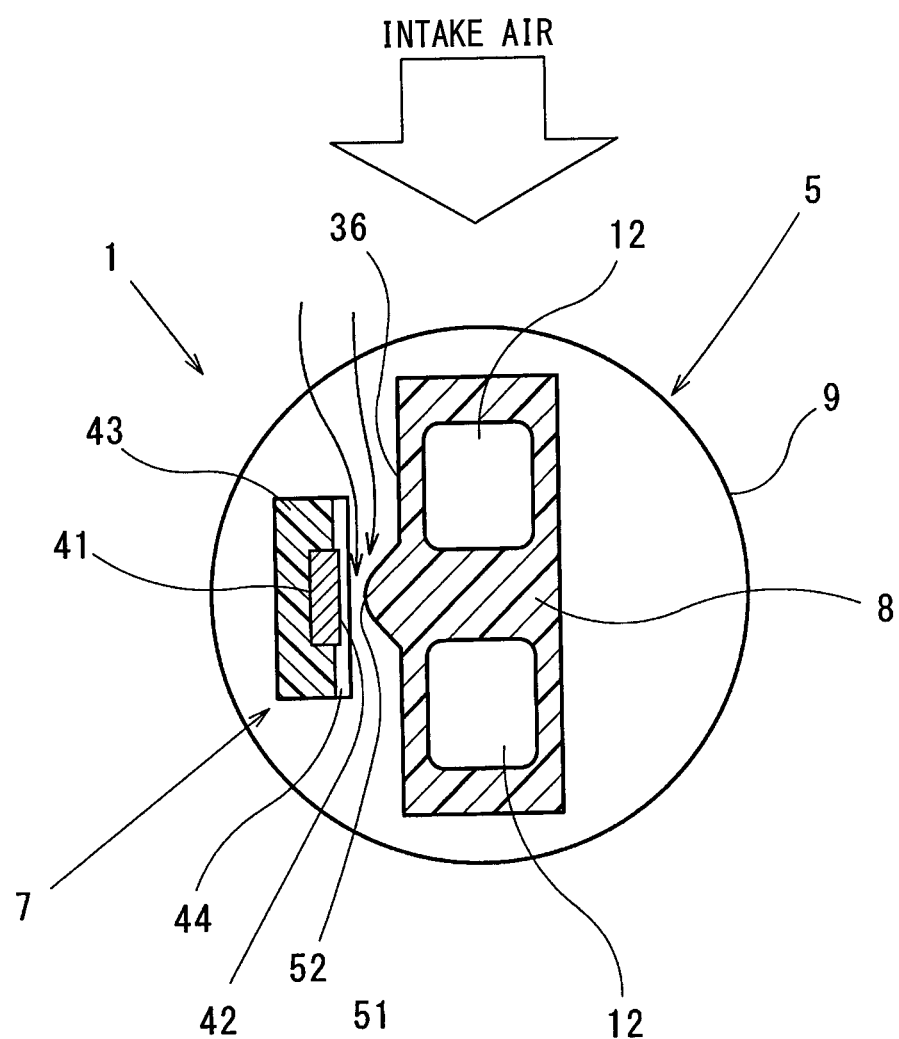
FIG. 12 is a view illustrating a flow of air passing through a clearance (of the third embodiment).

FIG. 10 through FIG. 12 illustrate a third embodiment.

The same mark as the first and second embodiments indicates the same configuration or function, and the redundant explanation is omitted.

The outer wall 36 of the case 5 of this embodiment has an opposing surface 51 which opposes the surface 42 of the sensing part 41. The opposing surface 51 has a projection 52 projected toward the surface of the sensing part 41. The projection 52 is formed in a curved surface shape or a sphere surface shape. Moreover, the projection 52 forms a choke part which partially decreases the passage sectional area in the passage outside of the case 5. The passage outside of the case 5 represents the clearance S formed between the outer wall 36 of the case 5 and the surface 42 of the sensing part 41.

The distance between the surface 42 of the sensing part 41 and the outer wall 36 can be further narrowed than the first and second embodiments by the projection 52. Thereby, the flow velocity of intake air increases compared with the first embodiment, and the scavenging speed of the intake air becomes high immediately the surface 42 of the sensing part 41, such that the humidity responsivity of the sensing part 41 becomes high.

As mentioned above, the same effect can be obtained in the air flow rate measurement device 1 of this embodiment as the first and second embodiments. In addition, the air flow rate measurement device 1 of this embodiment has the same sensor terminal structure and the same connector terminal structure as the first and second embodiments.

[Fourth Embodiment]

Figure 13:
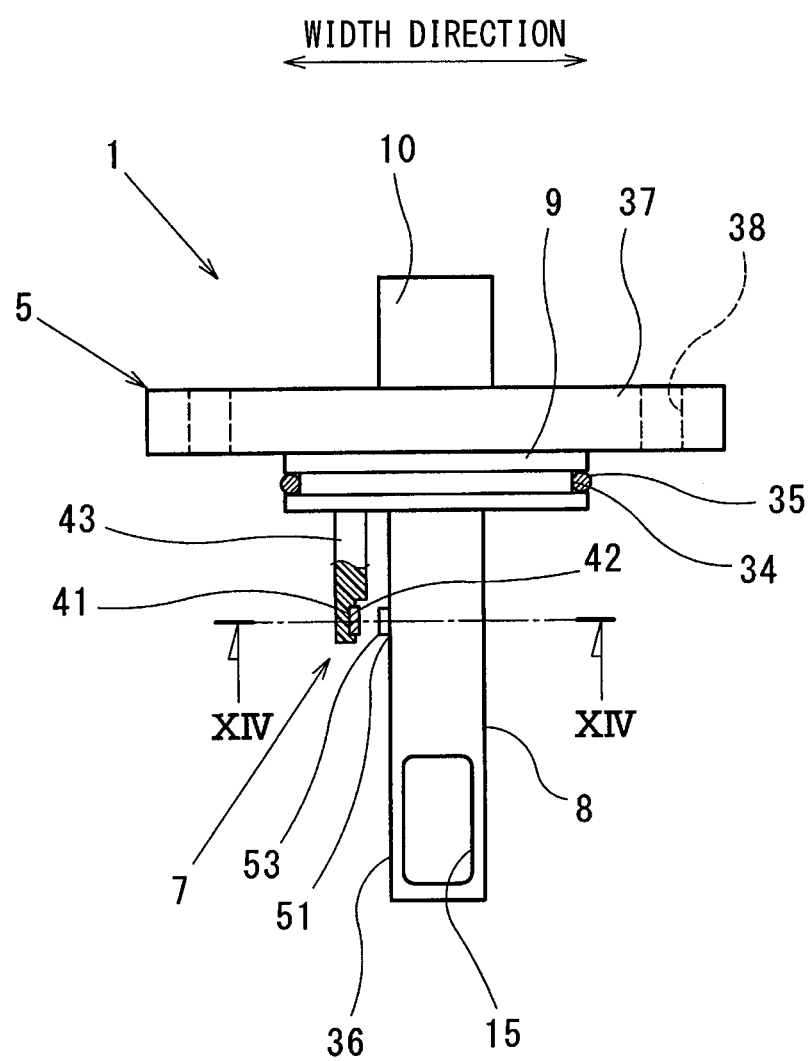
FIG. 13 is a front view illustrating an air flow rate measurement device (according to a fourth embodiment).
Figure 14:
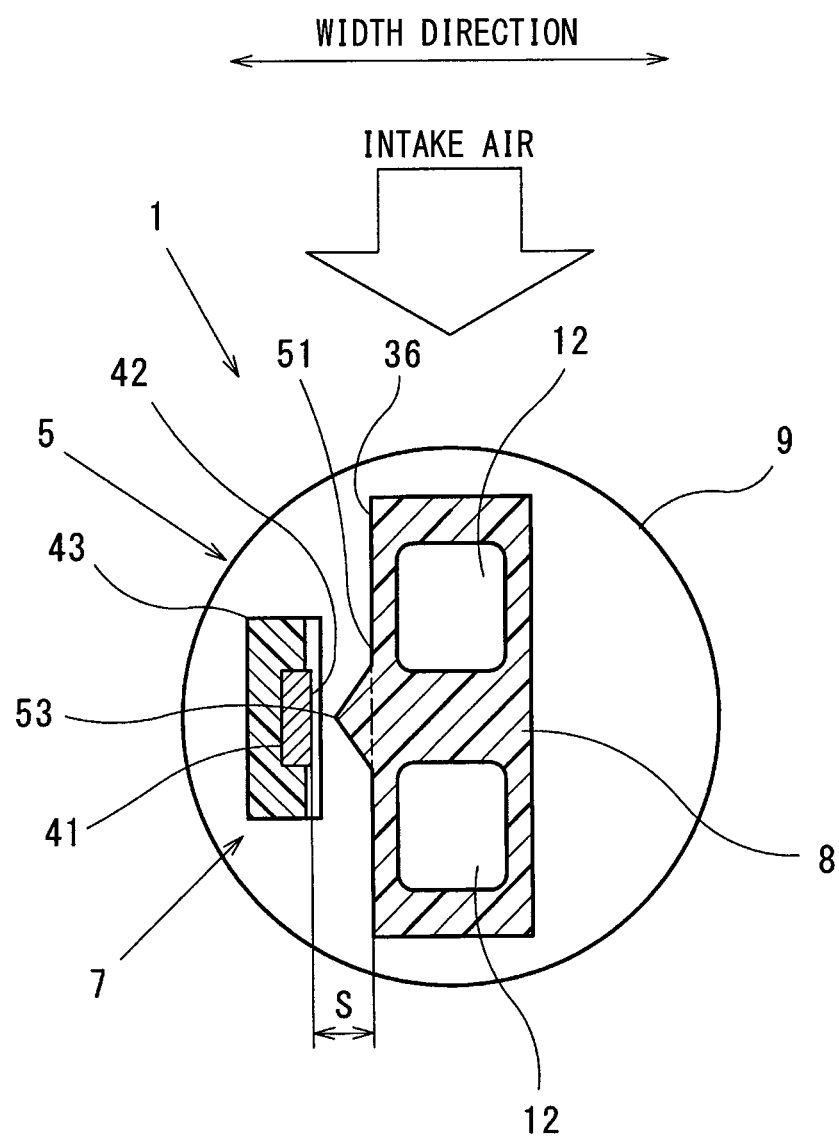
FIG. 14 is a sectional view taken along a line XIV-XIV of FIG. 13 (of the fourth embodiment).

FIG. 13 and FIG. 14 illustrate a fourth embodiment.

The same mark as the first to third embodiments indicates the same configuration or function, and the redundant explanation is omitted.

The outer wall 36 of the case 5 of this embodiment has an opposing surface 51 which opposes the surface 42 of the sensing part 41. The opposing surface 51 has a projection 53 projected toward the surface 42 of the sensing part 41. The projection 53 has a cone shape or a polygonal pyramid. Moreover, the projection 53 forms a choke part which partially decreases the passage sectional area in the passage outside of the case 5, similarly to the third embodiment.

As mentioned above, the same effect can be obtained in the air flow rate measurement device 1 of this embodiment as the first to third embodiments. In addition, the air flow rate measurement device 1 of this embodiment has the same sensor terminal structure and the same connector terminal structure as the first and second embodiments.

[Fifth Embodiment]

Figure 15:
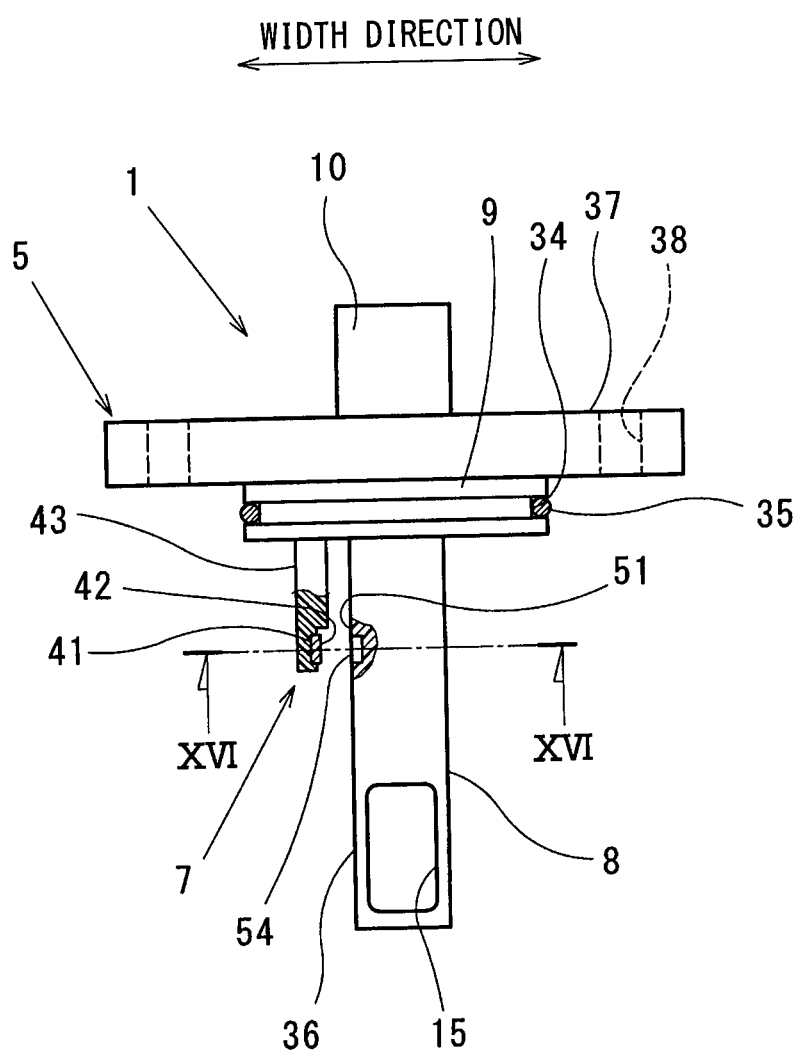
FIG. 15 is a front view illustrating an air flow rate measurement device (according to a fifth embodiment).
Figure 16:
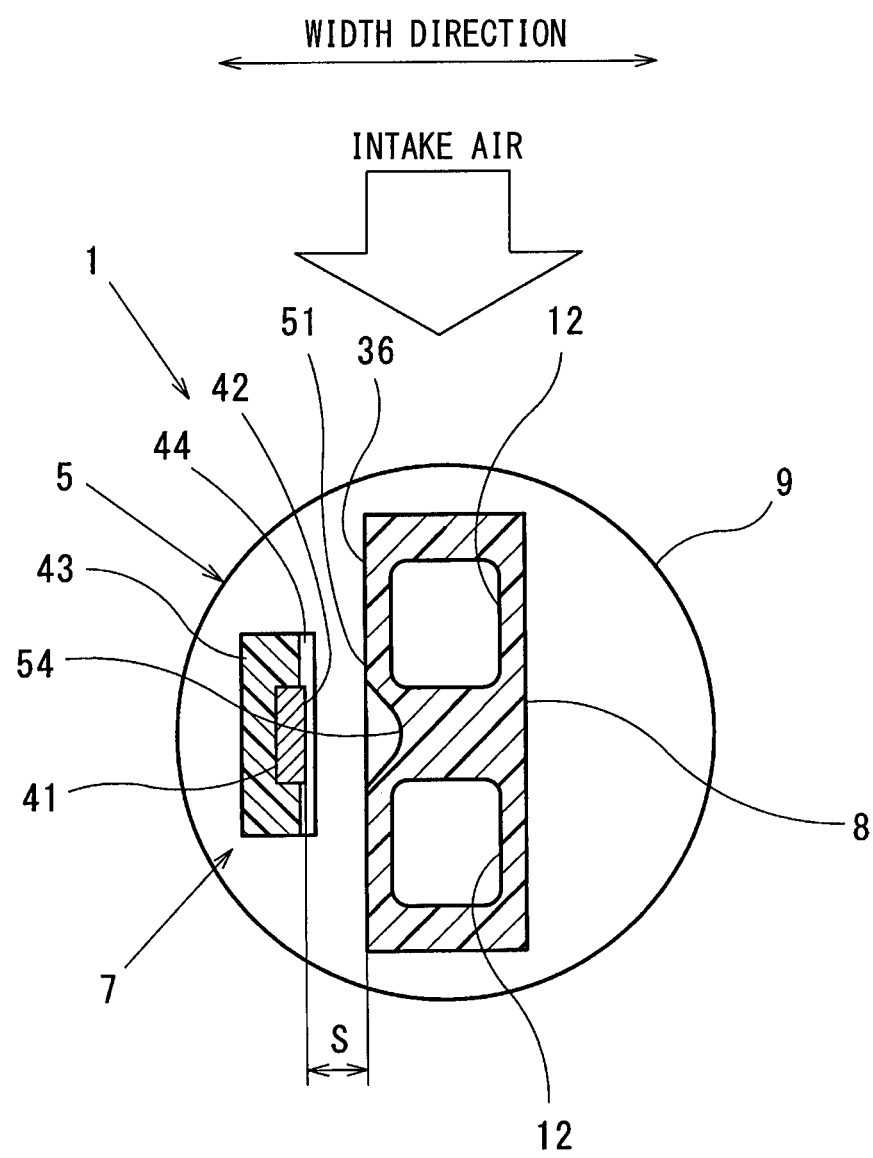
FIG. 16 is a sectional view taken along a line XVI-XVI of FIG. 15 (of the fifth embodiment).
Figure 17:
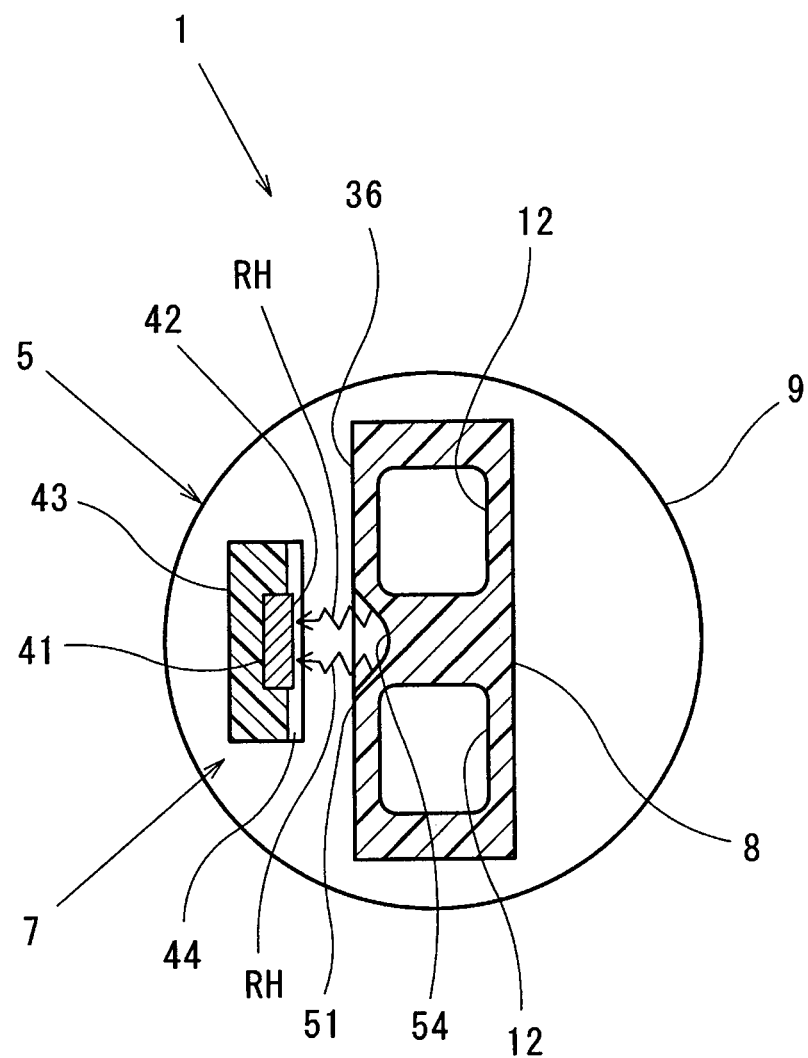
FIG. 17 is a view illustrating influence of radiant heat from an outer wall of a housing (of the fifth embodiment).

FIG. 15 through FIG. 17 illustrate a fifth embodiment.

The same mark as the first to fourth embodiments indicates the same configuration or function, and the redundant explanation is omitted.

The outer wall 36 of the case 5 of this embodiment has an opposing surface 51 which opposes the surface 42 of the sensing part 41. The opposing surface 51 has a recess 54 recessed to a side away from the surface of the sensing part 41.

The distance between the surface 42 of the sensing part 41 and the outer wall 36 is increased by the recess 54, compared with the first and second embodiments. Therefore, the rise in the air temperature caused by the radiant heat RH from the outer wall 36 is reduced, such that the detection error can be reduced in the humidity detected by the electric capacitance humidity sensor 7.

As mentioned above, the same effect can be obtained in the air flow rate measurement device 1 of this embodiment as the first to fourth embodiments. In addition, the air flow rate measurement device 1 of this embodiment has the same sensor terminal structure and the same connector terminal structure as the first and second embodiments.

[Sixth Embodiment]

Figure 18:
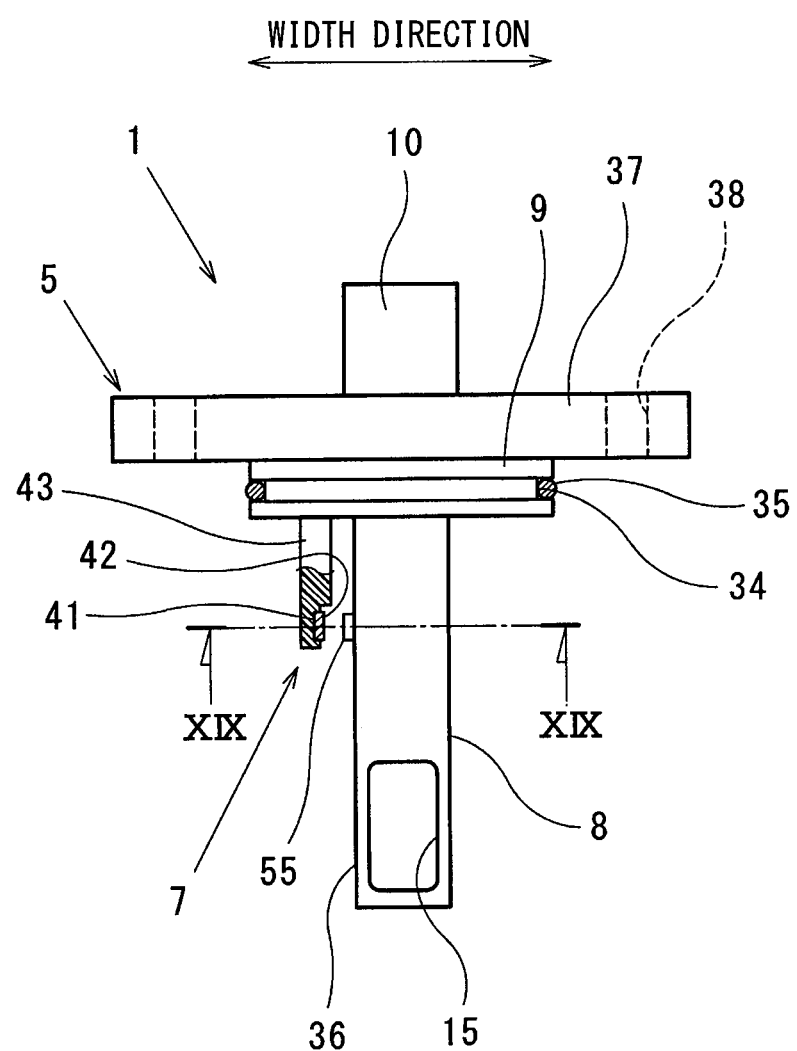
FIG. 18 is a front view illustrating an air flow rate measurement device (according to a sixth embodiment).
Figure 19:
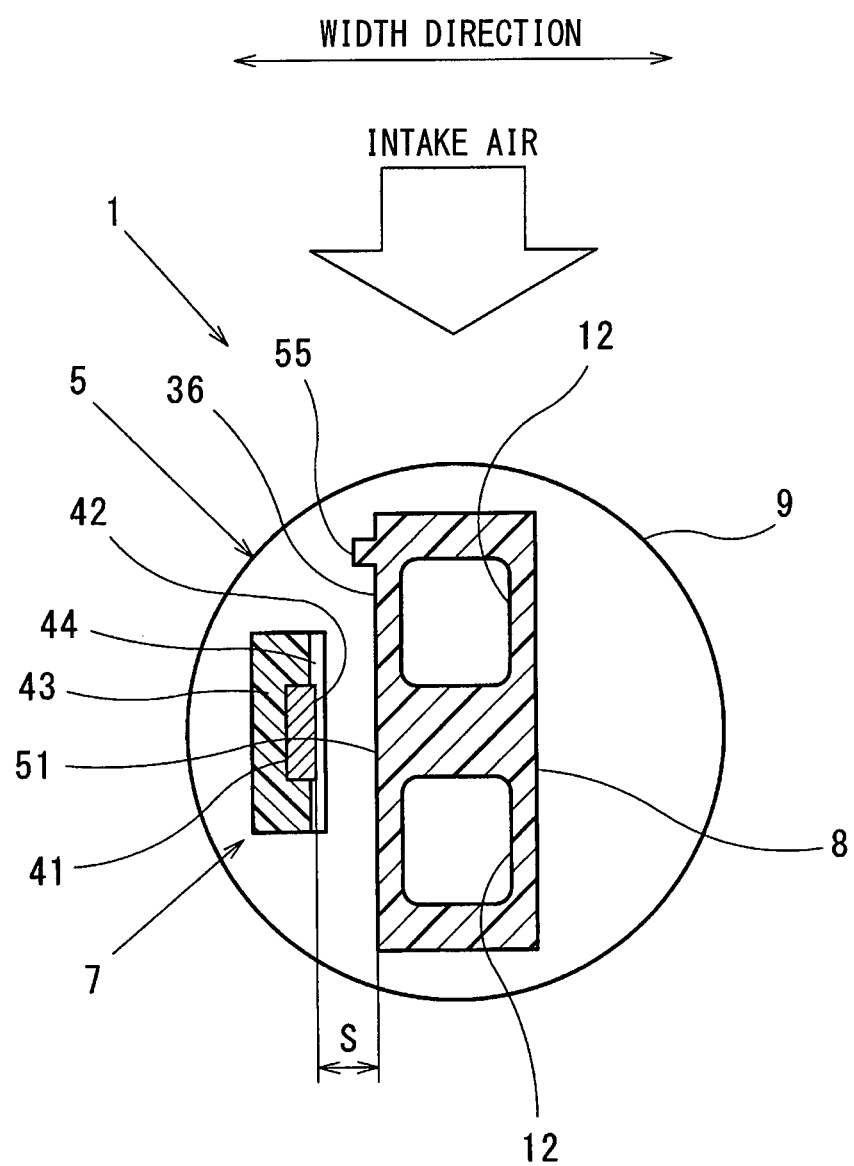
FIG. 19 is a sectional view taken along a line XIX-XIX of FIG. 18 (of the sixth embodiment).
Figure 20:
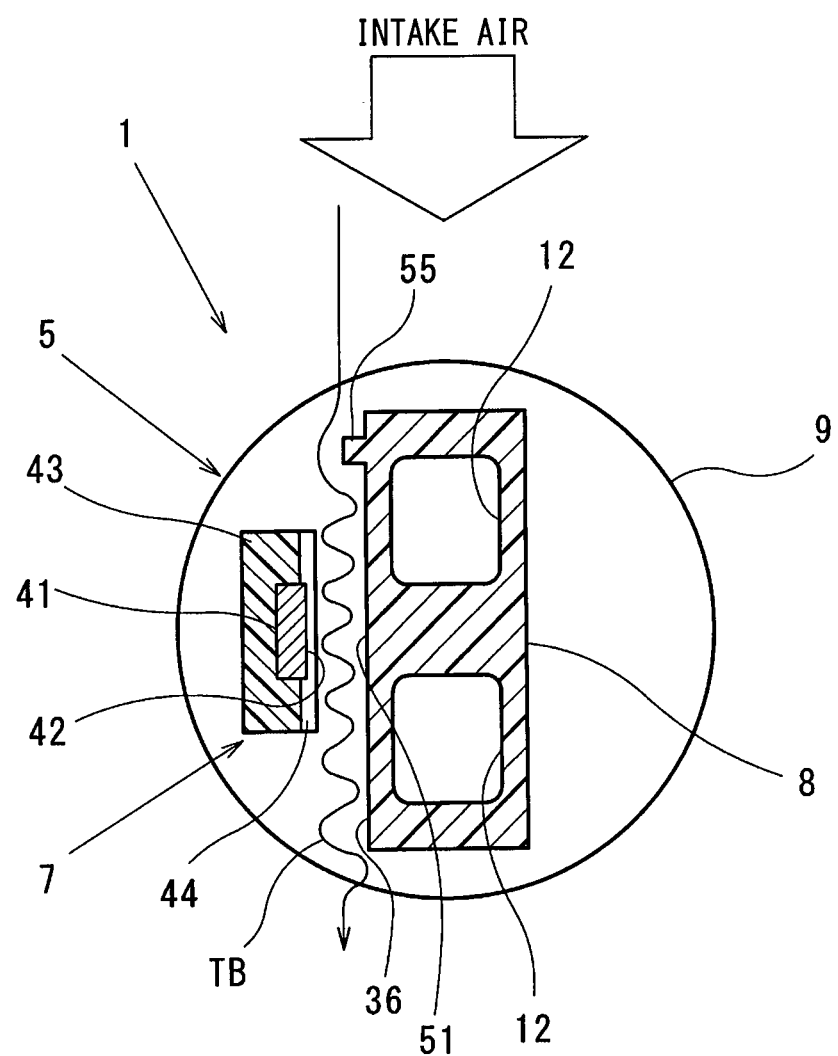
FIG. 20 is a view illustrating a flow of air passing through a clearance (of the sixth embodiment).

FIG. 18 through FIG. 20 illustrate a sixth embodiment.

The same mark as the first to fifth embodiments indicates the same configuration or function, and the redundant explanation is omitted.

The outer wall 36 of the case 5 of this embodiment has a projection 55 projected outward of the case 5 at the upstream side of the surface 42 of the sensing part 41.

Since a turbulent flow TB can be caused by the projection 55 to facilitate the scavenging, the humidity responsivity of the sensing part 41 becomes high.

As mentioned above, the same effect can be obtained in the air flow rate measurement device 1 of this embodiment as the first to fifth embodiments. In addition, the air flow rate measurement device 1 of this embodiment has the same sensor terminal structure and the same connector terminal structure as the first and second embodiments.

[Modification]

The thin-film heater resistance object and the thin-film air temperature resistance object formed in a predetermined pattern on a silicon substrate are adopted as the sensing part 21 of the flow rate sensor 6 in the embodiments. Alternatively, the sensing part 21 of the flow rate sensor 6 may have a heater resistance object and one or more air temperature resistance objects configured by a cylindrical bobbin, a pair of lead wires, a resistance wire, a protective film, and the like.

The pair of lead wires are components inserted at the both ends of the bobbin. The resistance wire is a component twisted around the perimeter of the bobbin and electrically connected to the lead wire. The protective film protects the resistance wire and the lead wire.

In the embodiments, the case 5 has the outer wall 36 on which air passes the outside, and the surface of the humidity detector (sensing part) 41 is disposed to oppose the outer wall 36 of the case 5 through the clearance S. Alternatively, the case 5 may have an inner wall on which air passes the inside, and the surface of the humidity detector may be disposed to oppose the inner wall of the case 5 through a clearance.

Moreover, the outer wall of the case 5 may have a streamline shape, a curved surface shape, or a plane shape. The outer wall of the case 5 may have a slope shape inclined to the flow direction of air flowing through the intake passage 4. The outer wall of the case 5 may be formed by a plane parallel to the flow direction of air flowing through the intake passage 4.

The present disclosure may be implemented with various modifications without being limited to the embodiments.

The invention claimed is:

1. An air flow rate measurement device disposed in an intake passage by passing through an insertion hole of an intake pipe of an engine to communicate inside and outside, the air flow rate measurement device comprising:
   a case having a bypass channel, wherein a part of air flowing through the intake passage flows into the bypass channel;
   a flow rate sensor arranged inside of the case, the flow rate sensor having a flow rate detector which detects a flow rate of air flowing through the bypass channel; and
   a humidity detector which detects a humidity of air flowing through the intake passage, wherein
   a surface of the humidity detector is located to oppose a wall of the case through a clearance, and
   the clearance is set within a range more than or equal to 0.5 mm and less than or equal to 10 mm.

2. The air flow rate measurement device according to claim 1, wherein
   the insertion hole has a hole width in a width direction perpendicular to a flow direction of air flowing through the intake passage, and
   the clearance is narrower than the hole width of the insertion hole.

3. The air flow rate measurement device according to claim 1, wherein
   the wall of the case has an opposing surface opposing the surface of the humidity detector, and
   the opposing surface has a projection projected toward the surface of the humidity detector.

4. The air flow rate measurement device according to claim 1, wherein
   the wall of the case has an opposing surface opposing the surface of the humidity detector, and
   the opposing surface has a recess recessed away from the surface of the humidity detector.

5. The air flow rate measurement device according to claim 1, wherein
   the wall of the case has a projection projected outward from the case at an upstream side of the surface of the humidity detector.

6. The air flow rate measurement device according to claim 1, wherein
   the flow rate sensor has a plurality of flow rate sensor terminals arranged to be parallel to a flow direction of air, and
   the humidity sensor has a plurality of humidity sensor terminals arranged to be parallel to a flow direction of air.

7. The air flow rate measurement device according to claim 6, further comprising:
   a plurality of connector terminals to be electrically connected with the plurality of flow rate sensor terminals and the plurality of humidity sensor terminals, wherein
   the case has one connector on which the plurality of connector terminals are arranged in a concentrated manner.

8. The air flow rate measurement device according to claim 1, wherein
   the case has an outer wall, and
   the surface of the humidity detector is disposed to oppose the outer wall of the case through the clearance.

9. The air flow rate measurement device according to claim 1, wherein
   the case has a support wall in which the humidity detector is supported, and
   the clearance is between the support wall and the wall of the case.

\* \* \* \* \*